United States Patent [19]

Bahrmann et al.

[11] Patent Number: 5,684,208
[45] Date of Patent: Nov. 4, 1997

[54] PROCESS FOR PREPARING PENTENALS

[75] Inventors: Helmut Bahrmann, Hamminkein; Peter Lappe, Dinslaken; Ernst Wiebus, Oberhausen; Bernhard Fell; Peter Hermanns, both of Aachen, all of Germany

[73] Assignee: Hoechst Aktiengesellschaft, Germany

[21] Appl. No.: 696,781

[22] Filed: Aug. 15, 1996

[30] Foreign Application Priority Data

Sep. 2, 1995 [DE] Germany .................. 195 32 394.7

[51] Int. Cl.$^6$ .................................................. C07C 45/50
[52] U.S. Cl. ................................ 568/454; 568/451
[58] Field of Search ........................... 568/454, 451

[56] References Cited

U.S. PATENT DOCUMENTS 4,248,802  2/1981  Kuntz et al. ..................... 568/454
5,434,312  7/1995  Fell et al. ........................ 568/454

FOREIGN PATENT DOCUMENTS 0033554   8/1981   European Pat. Off. .
0562450   9/1993   European Pat. Off. .
0643031   3/1995   European Pat. Off. .
2627354  12/1976   Germany .

*Primary Examiner*—Gary Geist
*Assistant Examiner*—Sreeni Padmanabhan
*Attorney, Agent, or Firm*—Bierman, Muserlian and Lucas, LLP

[57] ABSTRACT

In the process for hydroformylation of 1,3-butadiene with carbon monoxide and hydrogen to form pentenals, the improvement comprising effecting the hydroformylation with 1,3-butadiene dissolved in an inert reaction medium at 100° to 180° C. at 5 to 35 MPa in the presence of an aqueous solution of a rhodium/phosphine complex and optionally a further phosphine as catalyst.

17 Claims, No Drawings

PROCESS FOR PREPARING PENTENALS

STATE OF THE ART

As a by-product from crude oil refining, 1,3-butadiene is formed, for example, in a naphthapyrolysis as constituent of the $C_4$ fraction, a raw material available in large amounts for chemical syntheses. One way of utilizing it is the reaction with carbon monoxide and hydrogen (hydroformylation) to form carbonyl compounds and further reaction to form hydroxymethyl compounds. The hydroformylation of 1,3-butadiene has been widely studied. Owing to the presence of two conjugated double bonds, the reaction products to be expected are not only dialdehydes and monoaldehydes in their various structural isomeric forms, but also unsaturated $C_5$-aldehydes.

According to Fell et al, dialdehydes are formed in the hydroformylation of 1,3-butadiene in the presence of phosphine-modified rhodium catalysts (cf. Chem.-Ztg., Vol 99 (1975), 485 ff). The saturated $C_5$-monoaldehydes are obtained as reaction products in the hydroformylation in the presence of cobalt carbonyl catalysts, rhodium carbonyl catalysts or phosphine-modified rhodium carbonyl catalysts (cf. Fell et al, Forschungsbericht Bundesministerium Forschung und Technologie, BMFT-FB-T-84 064, Karlsruhe 1984).

In contrast to the synthesis of $C_5$-aldehydes and $C_6$-dialdehydes by reaction of butadiene with carbon monoxide and hydrogen, the hydroformylation of the 1,3-diolefin to give unsaturated $C_5$-aldehydes proceeds with only low selectivity. In the reaction of the reactants in a homogeneous reaction system with rhodium carbonyl/phosphine catalysts, pentanals are preferentially formed even under changing reaction conditions. Although the hydroformylation of 1,3-butadiene in the presence of water-soluble rhodium carbonyl/phosphine catalysts gives primarily n-penten-3-al as reaction product, the highly reactive unsaturated aldehyde is converted by aldol condensation into 2-propenylheptadienal and further into $C_{15}$- and higher molecular weight aldol products.

OBJECTS OF THE INVENTION

In view of the fact that unsaturated $C_5$-aldehydes are of great industrial interest as intermediates capable of undergoing numerous reactions because of the presence of the aldehyde function and a double bond in the molecule, it is an object of the invention to provide a process which allows the preparation of pentanals with high selectivity and yield.

This and other objects and advantages of the invention will become obvious from the following detailed description.

THE INVENTION

In the process for hydroformylation of 1,3-butadiene with carbon monoxide and hydrogen to form pentenals, the improvement comprises effecting the hydroformylation with 1,3-butadiene dissolved in an inert reaction medium at 100° to 180° C. at 5 to 35 MPa in the presence of an aqueous solution of a rhodium/phosphine complex and optionally a further phosphine as catalyst.

It has surprisingly been found that the selectivity of the conversion of 1,3-butadiene by hydroformylation in a heterogeneous reaction system is considerably improved if the 1,3-butadiene is not used as a pure substance, but is dissolved in a medium which is inert under the reaction conditions. The dilution of the diolefin leads, in particular, to avoidance of the subsequent reactions, viz. formation of aldol condensation products. Suitable inert media are, in particular, saturated aliphatic and cycloaliphatic hydrocarbons of 3 to 10 carbon atoms in the molecule and also aromatic hydrocarbons of 6 to 9 carbon atoms in the molecule. Examples of compounds of the classes mentioned are propane, n-butane, n-hexane, cyclohexane, toluene and the xylenes. The use of ethers as solvents for the 1,3-butadiene gives equally good results as does use of aliphatic or aromatic hydrocarbons. Representatives of ethers are, for example, diethyl ether or methyl tert-butyl ether.

It has been found to be advantageous for one part by volume of 1,3-butadiene to be dissolved in at least one part by volume of the inert medium. Preferably, one part by volume of 1,3-butadiene is dissolved in from one to ten parts by volume of the inert medium.

A particularly advantageous embodiment of the process of the invention comprises using 1,3-butadiene in the form of industrial hydrocarbon mixtures which mixtures are unavoidably obtained in considerable amounts, for example, as refinery by-products in the production of automobile fuel and in the preparation of ethylene by thermal cracking of higher hydrocarbons ($C_4$ cracking fractions). In addition to 1,3-butadiene and saturated $C_4$-hydrocarbons, they also contain n-but-1-ene, isobutene and cis- and trans-n-but-2-ene. Under the conditions of the butadiene hydroformylation, the olefins mentioned, with the exception of n-but-1-ene, are largely inert and together with the saturated $C_4$-hydrocarbons n- and i-butane form the inert medium in which the 1,3-butadiene is dissolved according to the invention.

The reaction of industrial hydrocarbon mixtures containing 1,3-butadiene in the process of the invention thus allows not only the preparation of olefinically unsaturated $C_5$-aldehydes, but in the context of a novel carborefining process leads to a raffinate comprising isobutene, cis- and trans-n-but-2-ene and the saturated $C_4$-hydrocarbons and contains only traces of 1,3-butadiene and n-but-1-ene. Isobutene can be separated from this mixture by known methods, e.g. by conversion into methyl tert-butyl ether. The remaining $C_4$-hydrocarbons are either recirculated to the pyrolysis process or chemically reacted in another way.

The hydroformylation of the 1,3-butadiene dissolved in the inert medium is carried out as a heterogeneous reaction in a two-phase system, a reaction which is described, for example, in DE-C 26 27 354. This process is distinguished by the presence of an organic phase which contains, inter alia, the olefinic compound and the reaction product and of an aqueous phase in which the catalyst is dissolved. The catalysts used are water-soluble rhodium complexes containing water-soluble organic phosphines as ligands. The water-soluble organic phosphine is usually present in excess, based on rhodium, i.e. not only the rhodium/phosphine complex but also free phosphine are present in the catalyst system.

For the purposes of the invention, the term "water-soluble, organic phosphines" means monophosphines or polyphosphines in which alkyls and/or aryls are bonded to the trivalent phosphorus atom or atoms, with at least one of these alkyls and/or aryls being singly or multiply sulfonated or carboxylated. The preparation of such phosphines is known and described, for example, in DE-C 26 27 354 and DD Patent 259 194.

Water-soluble organic phosphines which have been found to be particularly useful are compounds of the formula

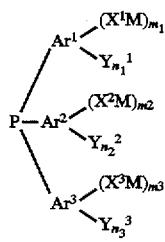

wherein $Ar^1$, $Ar^2$, $Ar^3$ are individually phenyl or naphthyl, $X^1$, $X^2$, $X^3$ are individually sulfonate ($-SO_3^-$) and/or carboxylate ($-COO^-$), $Y^1$, $Y^2$, $Y^3$ are individually selected from the group consisting of alkyl of 1 to 4 carbon atoms, alkoxy, halogen, $-OH$, $-CN$, $-NO_2$ and $(R^1R^2)N$ in which $R^1$ and $R^2$ are individually alkyl of 1 to 4 carbon atoms, $m_1$, $m_2$, $m_3$ are individually integers from 0 to 5, with the proviso that at least one $m_1$, $m_2$ or $m_3$ is greater than 0, $n_1$, $n_2$, $n_3$ are individually integers from 0 to 5, M is an alkali metal ion, one chemical equivalent of an alkaline earth metal ion or zinc ion, an ammonium or quaternary ammonium ion of the formula $N(R^3R^4R^5R^6)^+$ in which $R^3$, $R^4$, $R^5$, $R^6$ are individually hydrogen or alkyl of 1 to 4 carbon atoms.

Phosphines of Formula I which have been found to be particularly useful are those in which $Ar^1$, $Ar^2$, $Ar^3$ are each phenyl and $X^1$, $X^2$, $X^3$ are each sulfonate in the meta position relative to phosphorus, i.e. salts of tris(m-sulfonatophenyl)-phosphine (TPPTS).

The phosphine present in the catalyst system need not be uniform chemical compounds but can have different chemical compositions. Thus, they can differ, for example, in the type and bonding of the group attached to the phosphorus atom, in the degree of sulfonation or carboxylation or in the type of cations.

The catalyst system can be preformed before addition to the reaction mixture. However, equally good results are obtained by preparing it in the reaction mixture under reaction conditions from the rhodium or rhodium compound and the phosphine. Apart from metallic rhodium in finely divided form, it is possible to use rhodium salts such as rhodium(III) sulfate, rhodium(III) nitrate, rhodium(II) acetate, rhodium acetylacetonate, rhodium oxides or other carbonyl-forming compounds of rhodium as rhodium source.

The rhodium concentration in the aqueous catalyst phase is from 100 to 600 ppm by weight, preferably from 300 to 500 ppm by weight, based on the solution. The phosphine is usually used in such an amount that at least 20 moles, preferably from 40 to 80 moles, of P(III) are present per mole of rhodium. The reaction of 1,3-butadiene with hydrogen and carbon monoxide is carried out at temperatures of from 100° to 180° C., preferably from 110° to 120° C., and pressures of from 5 to 35 MPa, preferably from 4 to 8 MPa.

The pH of the catalyst solution is from 4 to 10, preferably from 5.5 to 9.

The ratio of carbon monoxide to hydrogen in the synthesis gas can be varied within wide limits. In general, the synthesis gas used is one in which the volume ratio of carbon monoxide to hydrogen is 1:1 or deviates only little from this value.

The volume ratio of catalyst phase to organic phase can be varied in the range of 1:4 to 4:1, with a ratio of from 1:1 to 2:1 being advantageous.

The reaction can be carried out either batchwise or continuously.

The reaction product is worked up by separating the organic phase and the aqueous catalyst phase from one another. The hydroformylation products are isolated by distillation from the catalyst phase.

In the following examples, there are described several preferred embodiments to illustrate the invention. However, it is to be understood that the invention is not intended to be limited to the specific embodiments.

EXAMPLE 1

(Comparative Example)

A 160 ml V4A stainless steel autoclave fitted with a pressure-resistant metering vessel, a pressure sensor, a bursting disk, a thermocouple and a magnetically coupled propellant stirrer was charged with 40 g of an aqueous catalyst solution of 16.4 mg of rhodium (in the form of an aqueous rhodium(III) sulfate solution), corresponding to 410 ppm of Rh in the solution, and 3.77 g of $Na_3$-TPPTS under an argon atmosphere. The pH was adjusted to 6 by addition of $Na_2CO_3$ and the autoclave was closed. 20 g of 1,3-butadiene from a pressure gas bottle were then condensed into an evacuated metal capillary provided with two valves. As internal standard for gas-chromatographic analysis (GC analysis), a weighed amount of propane was additionally added. The metal coil containing the 1,3-butadiene/propane sample was screwed onto the metering vessel and the catalyst solution was added after flushing the autoclave with water gas ($CO/H_2=1/1$) preformed for 90 minutes at 110° C. and 10 MPa. The desired reaction pressure for the hydroformylation, viz. 6 MPa, was then set in the autoclave. The liquefied gas in the metal coil was injected into the intensively stirred autoclave and the reaction was thereby started. After a reaction time of 5 hours, the reaction mixture was cooled, and the amount and composition of the gas phase was measured for determining the conversion. The aqueous catalyst phase, after separating off the organic reaction product, was extracted three times with 15 ml each time of diethyl ether. The solution of the reaction product in the ether was dried over $Na_2SO_4$ and then was analyzed by gas chromatography.

| Result: | |
|---|---|
| Conversion: | 89% |
| Composition: | |
| n-Pentenals/n-pentanal | 34% |
| 2-Propenylhepatadienal | 34% |
| 2-Methylbutanal | 2% |
| Other products*) | 11% |
| Stand oil (>$C_{10}$) | 19% |

*)This was mainly formylcyclopentene, the intramolecular aldol condensation product of 1,6-hexanedial which was formed by hydroformylation of n-penten-4-al. Very small amounts of 2-methyl-pentanedial and ethylbutanedial are also formed as further bis-hydroformylation products.

EXAMPLE 2

1,3-Butadiene was reacted in the presence of diethyl ether as solvent (volume ratio of solvent/butadiene=2) under the conditions of Example 1, but with the reaction time shortened to 4 hours.

| Result: | |
|---|---|
| Conversion: | 82% |
| Composition: | |
| n-Pentenals/n-pentanal | 85% |
| 2-Propenylheptadienal | 1.5% |
| 2-Methylbutanal | 1.5% |
| Other products | 10% |
| Stand oil (>$C_{10}$) | 2% |

Composition of the n-pentenals/n-pentanal fraction: 72% of cis/trans 3-pentenal, 3% of 4-pentenal, 1% of 2-pentenal and 23% of n-pentanal.

EXAMPLES 3 TO 6

The experiments described in the Examples 3 to 12 below were carried out using a $C_4$ fraction obtained by pyrolysis of naphtha and having the following composition:

| | |
|---|---|
| 1,3-Butadiene | 46% |
| i-Butene | 23.5% |
| n-But-1-ene | 11.5% |
| trans-n-But-2-ene | 5% |
| cis-n-But-2-ene | 4% |
| 1,2-Butadiene, butenyne, butyne | 1% |
| n-Butane | 6% |
| i-Butane | 3% |

In Examples 3 TO 6, the reaction temperature and the reaction time were varied, and the starting material (20 g of $C_4$ fraction) and the other reaction conditions were the same as those of Example 1.

Examples 3 to 6:
Composition of the reaction products (% by weight)

| Ex. | Reaction Temp. °C. | Time h | n-Pentenals/ n-Pentanal* | 2-Propenyl- heptadienal | 2- Methyl- butanal | 3- | Formyl- cyclo- pentene | Stand oil (>C10) | Remainder** |
|---|---|---|---|---|---|---|---|---|---|
| 3 | 200 | 6 | 67(49) | 6 | 3 | 1 | 6 | 5 | |
| 4 | 110 | 4 | 68(62) | 9 | 4 | 1 | 7 | 2 | |
| 5 | 120 | 2 | 69(73) | 6 | 4 | 1 | 6 | 3 | |
| 6 | 120 | 12 | 57(18) | 10 | 5 | 6 | 8 | 2 | |

*The proportion of cis/trans-n-penten-3-al in the $C_5$ fraction is shown in brackets
**The remainder to 100% comprised various unidentified compounds containing less than 10 carbon atoms in the molecule.

Examples 3 to 6:
Conversion of the $C_4$ constituents of the starting material (% by weight)

| Example | 1,3-Butadiene | n-But-1-ene | cis- n-But-2-ene | trans- n-But-2-ene | i-Butene |
|---|---|---|---|---|---|
| 3 | 90 | 63 | 10 | 7 | 11 |
| 4 | 91 | 79 | 5 | <1 | 11 |
| 5 | 91 | 69 | 1 | 0 | 9 |
| 6 | 94 | 93 | 23 | 5 | 24 |

EXAMPLES 7 TO 9

In Examples 7 to 9, the hydroformylation of the $C_4$ fraction was carried out with variation of the P/Rh ratio in the aqueous catalyst solution. The other conditions were the same as those in Example 1, with the exception of the reaction time which was 4 hours.

Examples 7 to 9:
Composition of the reaction products (% by weight)

| Ex. | P/Rh ratio | n-Pentenals/ n-Pentanal* | 2-Propenyl- heptadienal | 2- Methyl- butanal | 3- Formyl- cyclopentene | Stand oil (>C10) | Remainder** |
|---|---|---|---|---|---|---|---|
| 7 | 10 | 63(66) | 6 | 4 | <1 | 7 | 9 |
| 8 | 40 | 68(62) | 9 | 4 | 1 | 7 | 2 |
| 9 | 60 | 68(59) | 10 | 3 | 1 | 6 | 3 |

*The proportion of cis/trans-n-penten-3-al in the $C_5$ fraction is shown in brackets
**The remainder to 100% comprised various unidentified compounds containing less than 10 carbon atoms in the molecule.

Examples 7 to 9:
Conversion of the $C_4$ constituents of the starting material (% by weight)

| Example | 1,3-Butadiene | n-But-1-ene | cis- n-But-2-ene | trans- | i-Butene |
|---|---|---|---|---|---|
| 7 | 80 | 34 | 1 | 0 | 5 |
| 8 | 92 | 79 | 5 | 0 | 11 |
| 9 | 91 | 68 | 12 | 9 | 19 |

EXAMPLES 10 TO 12

Examples 10 to 12 show the influence of the pH of the aqueous catalyst phase on the hydroformylation of the $C_4$ fraction. These examples were again carried out under the reaction conditions given for Example 1, but with the reaction time being shortened to 4 hours.

Example 10 to 12:
Composition of the reaction products (% by weight)

| Ex. | pH | n-Pentenals/ n-Pentanal* | 2-Propenyl- heptadienal | 2- Methyl- butanal | 3- Formyl- cyclopentene | Stand oil (>C10) | Remainder** |
|---|---|---|---|---|---|---|---|
| 10 | 5 | 81(65) | 2 | 3 | 1 | 6 | <1 |
| 11 | 7 | 74(64) | 5 | 3 | 1 | 7 | 3 |
| 12 | 9 | 68(62) | 9 | 4 | 1 | 7 | 2 |

*The proportion of cis/trans-penten-3-al in the $C_5$ fraction is shown in brackets
**The remainder to 100% comprised various unidentified compounds containing less than 10 carbon atoms in the molecule.

Various modifications of the process of the invention may be made without departing from the spirit or scope thereof and it is to be understood that the invention is intended to be limited only as defined in the appended claims.

What we claim is:

1. In the process for heterogeneous hydroformylation of 1,3-butadiene with carbon monoxide and hydrogen to form pentenals, the improvement comprising effecting the hydroformylation with 1,3-butadiene dissolved in an inert reaction medium at 100° to 180° C. at 5 to 35 MPa in the presence of an aqueous solution of a rhodium/phosphine complex and optionally a further phosphine as catalyst.

2. The process of claim 1 wherein the inert medium is a member of the group consisting of aliphatic and cycloaliphatic hydrocarbons of 3 to 10 carbon atoms and aromatic hydrocarbons of 6 to 9 carbon atoms.

3. The process of claim 1 wherein the inert medium is an ether.

4. The process of claim 1 wherein the solution of 1,3-butadiene in an inert medium is a mixture of $C_4$-hydrocarbons obtained in the refining of crude oil.

5. The process of claim 1 wherein 1 part by volume of the 1,3-butadiene is dissolved in at least 1 part by volume of the inert medium.

6. The process of claim 5 wherein 1 part by volume of the 1,3-butadiene is dissolved in from 1 to 10 parts by volume of the inert medium.

7. The process of claim 1 wherein the rhodium/phosphine complex contains a monophosphine of the formula

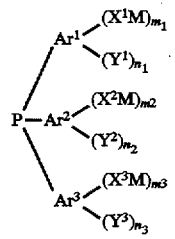

where $Ar^1$, $Ar^2$, $Ar^3$ are individually phenyl or naphthyl, $X^1$, $X^2$, $X^3$ are individually a sulfonate ($-SO_3^-$) and/or carboxylate ($-COO^-$) $Y^1$, $Y^2$, $Y^3$ are individually selected from the group consisting of alkyl of 1 to 4 carbon atoms, alkoxy, halogen, $-OH$, $-CN$, $-NO_2$ and $(R^1R^2)N$ wherein $R^1$ and $R^2$ are individually alkyl of 1 to 4 carbon atoms, $m_1$, $m_2$, and $m_3$ are individually integers from 0 to 5, with the proviso that at least one $m_1$, $m_2$, or $m_3$ is greater than 0 and $n_1$, $n_2$, $n_3$ are individually integers from 0 to 5, M is selected from the group consisting of an alkali metal ion, one chemical equivalent of an alkaline earth metal ion or zinc ion, an ammonium and quaternary ammonium ion of the formula $N(R^3R^4R^5R^6)^+$ in which $R^3$, $R^4$, $R^5$, $R^6$ are individually hydrogen or alkyl of 1 to 4 carbon atoms.

8. The process of claim 7 wherein the rhodium/phosphine complex contains a tris(m-sulfonatophenyl)phosphine salt.

9. The process of claim 1 wherein the reaction is carried out at 110° to 120° C. and at 4 to 8 MPa.

10. The process of claim 1 wherein the rhodium concentration in the aqueous catalyst solution is from 100 to 600 ppm by weight, based on the solution.

11. The process of claim 1 wherein at least 20 moles of P(III) in the form of a phosphine are present per mole of rhodium.

12. The process of claim 1 wherein the pH of the aqueous catalyst solution is from 4 to 10.

13. The process of claim 12 wherein the pH of the aqueous catalyst solution is from 5.5 to 9.

14. The process of claim 1 wherein the volume ratio of aqueous to organic phase is from 1:4 to 4:1.

15. The process of claim 14 wherein the volume ratio of aqueous to organic phase is from 1:1 to 1:2.

16. The process of claim 11 wherein 40 to 80 moles of P(III) in the form of phosphine are present per mole of rhodium.

17. The process of claim 10 wherein the rhodium concentration in the aqueous catalyst solution is 300 to 500 ppm by weight, based on the solution.

\* \* \* \* \*